United States Patent [19]

Marhold

[11] Patent Number: 4,914,244
[45] Date of Patent: Apr. 3, 1990

[54] PROCESS FOR PREPARING DIFLUOROCHLOROMETHOXYBENZENES

[75] Inventor: Albrecht Marhold, Leverkusen, Fed. Rep. of Germany

[73] Assignee: Bayer Aktiengesellschaft, Leverkusen, Fed. Rep. of Germany

[21] Appl. No.: 3,096

[22] Filed: Jan. 14, 1987

[30] Foreign Application Priority Data

Jan. 30, 1986 [DE] Fed. Rep. of Germany ....... 3602681

[51] Int. Cl.$^4$ ...................... C07C 43/225; C07C 41/00
[52] U.S. Cl. ...................................... 568/585; 560/18; 560/59; 560/65; 558/423; 558/424; 568/44; 568/49; 568/53; 568/637; 568/642; 568/643; 568/655; 568/656; 568/586
[58] Field of Search ................. 568/53, 585, 586, 655, 568/656, 637, 642, 643, 44, 49; 560/59, 65, 18; 260/543 F, 643 R, 544 P; 558/423, 424

[56] References Cited

U.S. PATENT DOCUMENTS 3,213,062  10/1965  Ellingboe ........................ 560/227 X

FOREIGN PATENT DOCUMENTS 0052558   5/1982  European Pat. Off. .
0168344   1/1986  European Pat. Off. .
0196529  10/1986  European Pat. Off. .
0199660  10/1986  European Pat. Off. .

OTHER PUBLICATIONS

Weygard, Preparation Organic Chemistry, John Wiley & Sons, N.Y., 1972, pp. 378–379.
Ramsperger et al., J. Amer. Chem. Soc., vol. 55, pp. 214–217, Jan. 1933.
Houben—Weyl "Methoden der Organischen Chemie, Band E4: Kohlensaure-Derivative", 4th Edition, 1983, Georg Thieme Verlag, Stuttgart—New York Seiten 626–628, 1204.

*Primary Examiner*—Werren B. Lone
*Attorney, Agent, or Firm*—Sprung Horn Kramer & Woods

[57] ABSTRACT

Difluorochloromethoxybenzenes are prepared by reacting phenols with trichloromethyl chloroformate (=diphosgene) in the presence of hydrogen fluoride.

11 Claims, No Drawings

PROCESS FOR PREPARING DIFLUOROCHLOROMETHOXYBENZENES

BACKGROUND OF THE INVENTION

Field of the Invention

The present invention relates to a process for preparing difluorochloromethoxybenzenes from phenols.

Background Information

It is already known that difluorochloromethoxybenzenes can be prepared by reacting trichloromethoxybenzenes in stages with a fluorinating agent, for example hydrogen fluoride or antimony trifluoride (see Houben-Weyl, 4th edition, volume E4, page 628 (1983)).

The disadvantage of this known method is that it requires a starting material which in turn must be prepared in an at least a 2-stage process from phenols, namely by a methylation and an optionally multistage side chain chlorination. In addition, if, for example, ring-brominated methoxybenzenes are used in this process, the ring bromine atoms are split-off in the course of the chlorination and replaced by chlorine, and nitroanisoles cannot be chlorinated at all in the methoxy group.

It is further known that phenols can be converted with tetrachloromethane and hydrogen fluoride into trifluoromethoxybenzenes (see Houben-Weyl, 4th edition, volume E4, page 626 (1983)).

This process requires relatively high temperatures. If in the process the tetrachloromethane is replaced by fluorotrichloromethane, it is found that fluorotrichloromethane is even less reactive and requires even higher temperatures and/or a catalyst. Difluorochloromethoxybenzenes can in both cases be obtained only in small yields.

Finally, it is known of trichloromethyl chloroformate, which is hereinafter also referred to as diphosgene, that, in the presence of acidic substances, it is cleaved into 2 moles of phosgene even at 20° C. and in the presence of active carbon it decomposes into carbon dioxide and tetrachloromethane (see Houben-Weyl, volume 4E, page 1204 (1983)). Diphosgene thus tends to decompose even at low temperatures.

SUMMARY OF THE INVENTION

We have now found a process for preparing difluorochloromethoxybenzenes from phenols, which is characterized in that phenols are reacted with trichloromethyl chloroformate in the presence of hydrogen fluoride.

DETAILED DESCRIPTION OF THE INVENTION

In the process according to the invention, it is possible to use, for example, those phenols which conform to the formula (I)

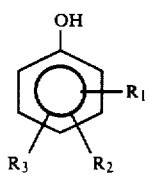

(I)

in which $R_1$, $R_2$ and $R_3$ are identical or different and each stands for hydrogen, halogen, alkyl, aryl, O-aryl or S-aryl.

In the formula, preferably one or two of the radicals $R_1$ to $R_3$ stand for hydrogen.

Halogen can be for example fluorine, chlorine, bromine or iodine, preferably fluorine, chlorine or bromine. Alkyl can be for example $C_1$- to $C_4$-alkyl, preferably methyl. Aryl, O-aryl and S-aryl can contain, for example, 6 to 8 C atoms and can be optionally substituted in the aryl part, for example by $NO_2$, CN, COHal (where Hal is a halogen, for example, fluorine), COOalkyl (with, for example, $C_1$- to $C_4$-alkyl), $SO_2F$, $SO_2Cl$, alkyl (for example, $C_1$- to $C_4$-alkyl), halogen (for example, fluorine, chlorine and/or bromine), alkoxy (for example, $C_1$- to $C_4$-alkoxy) and/or halogenoalkyl (for example, fluoro-, chloro-and/or bromo-$C_1$- to $C_4$-alkyl).

Particularly preferably $R_1$ and $R_2$ stand for hydrogen and $R_3$ for methyl, fluorine, chlorine, bromine, $C_6$-aryl or O-$C_6$aryl, where the aryl groups optionally contain one of the abovementioned substituents and the radical $R_3$ is in the meta or para position relative to the phenolic OH group in the case of aryl or O-aryl.

Very particularly preferred phenols of the formula (I) are 4-chlorophenol, 4-bromophenol, 2-chlorophenol, 2-bromophenol, 2-fluorophenol, 3-fluorophenol, 4-fluorophenol, 3-bromophenol, 4-(4-nitro-2,6-dimethylphenoxy)-phenol, 4-(4-nitro-2,5-dimethylphenoxy)-phenol, 4-(4-nitro-2-chloro-6-methylphenoxy)-phenol, 4-(4-nitro-2-chlorophenoxy-phenol 4-(4-nitro-2-chlorophenoxy)-2-chlorophenol, 4-(4-bromophenyl)-phenol and 4-(4-nitrophenyl)-phenol and 4-(4-nitro-6-methylphenoxy)-phenol.

The diphosgene can be used in commercially available grades or be prepared from methyl formate and/or methyl chloroformate by chlorination. Stoichiometrically, 1 mole of diphosgene is required per mole of phenol used. In general at least 1 mol of diphosgene is therefore used per mol of phenol. Preferably, however, the diphosgene is used in molar excess, for example 1.01 to 5 moles of diphosgene per mol of phenol.

Hydrogen fluoride is generally used in excess and can at the same time also serves as the solvent for the reaction according to the invention. For example, 5 to 100 moles of hydrogen fluoride can be used per mole of phenol. Preferably 8 to 40 moles of hydrogen fluoride are used per mol of phenol. The hydrogen fluoride can be, for example, of technical-grade, anhydrous quality.

In addition to hydrogen fluoride it is also possible to use an inert solvent, for example, dichloromethane, dichloroethane, a chlorinated aromatic, for example, chlorobenzene, or a reaction product from the process according to the invention.

Likewise in addition to hydrogen fluoride, it is possible to use a Friedel-Crafts catalyst, for example, titanium tetrachloride.

The addition of the reactants and, if used, of the auxiliary substances can be effected in any desired manner and in any desired order. Preferably, if relatively low reaction temperatures are employed at the start of the reaction, it is ensured that an excess of diphosgene is present, for example, by adding the phenol, if desired together with the hydrogen fluoride, solvent and/or catalyst, to initially introduced diphosgene. In the case of relatively high reaction temperatures at the start of the reaction, it is preferred to introduce the hydrogen fluoride first, if desired together with the phenol, the solvent and/or the catalyst, and to add diphosgene, or to meter phenol and diphosgene simultaneously into initially introduced hydrogen fluoride.

The process according to the invention can be carried out at various temperatures, for example at $-10°$ to $+100°$ C. Preferred temperatures are those from $0°$ to $60°$ C., particularly preferred those from $5°$ to $50°$ C. The process according to the invention can also be carried out at room temperature, for example $15°$ to $25°$ C., and to dispense with heating and cooling. It is also possible to vary the temperature during the reaction, for example, to start the reaction at $-5°$ to $+20°$ C. and to complete the reaction at a temperature which is $5°$ to $20°$ C. higher than the starting temperature.

The reaction according to the invention is in general complete when there is no further evolution of hydrogen chloride. Advantageously, the reaction mixture is held at the reaction temperature for some more time after the evolution of hydrogen chloride has ceased. Suitable reaction times are for example those between 1 and 30 hours.

The reaction mixture then present can be worked-up in a simple manner. It is possible, for example, first to remove excess hydrogen fluoride and, if desired, solvent, for example by distillation. The residue left behind, or even the reaction mixture as a whole, can be discharged, for example, into ice-water and the resulting precipitate be filtered-off and, if necessary, further purified. It is also possible to subject the residue left after removing excess hydrogen fluoride and, if desired, solvent to a fractional distillation, preferably at reduced pressure.

The process according to the invention has for example the advantages that it permits the preparation of difluorochloromethoxybenzenes at low temperatures from readily accessible starting materials and in high yields and selectivities.

It is extremely surprising that these advantages can be obtained, since it had to be expected that the diphosgene is decomposed in the presence of hydrogen fluoride before it (the diphosgene) can react with phenols.

The difluorochloromethoxybenzenes prepared by the process according to the invention can, even without isolation from the reaction mixture, be reacted, for example, with a fluorinating agent, such as hydrogen fluoride, to give the corresponding trifluoromethoxybenzenes, from which it is possible to prepare by nitration, reduction and reaction with isocyanates, ureas which are insecticidally and/or herbicidally active substances (see for example EP-A-No. 57,888, EP-A-No. 93,976, EP-A-No. 93, 977, EP-A-No. 132,680 and EP-A-No. 122,449).

EXAMPLES

General method

A stainless steel fluorination apparatus was charged with hydrogen fluoride, followed by the particular phenol and then, at the indicated temperature, dropwise and with stirring, by diphosgene. A marked evolution of hydrogen chloride began immediately.

After the evolution of gas had ceased, first excess hydrogen fluoride, if desired together with solvent used, was recovered by distillation at atmospheric pressure. Subsequently the reaction product was distilled-off under reduced pressure.

This method was used to carry out the individual experiments listed in Table 1.

TABLE 1

| Example No. | Amount of HF | Phenol used | Amount of diphosgene | Reaction time | Reaction temperature | Reaction product (-difluorochloro-methoxybenzene) |
|---|---|---|---|---|---|---|
| 1 | 300 g | 4-chlorophenol 60 g | 130 g | 9 hours | 10–20° C. | 4-chloro- 56 g |
| 2 | 300 g | 4-bromphenol 80 g | 275 g | 25 hours | 10–20° C. | 4-brom- 77 g |
| 3 | 300 g | 2-bromphenol 80 g | 130 g | 5 hours | 20° C. | 2-brom- 48 g |
| 4 | 200 g + 100 ml CH$_2$Cl$_2$ | 4-(4-nitro-,2,6-dimethyl-phenoxy) -phenol 50 g | 80 g | 6 hours | 20–50° C. | 4-(4-nitro-2,6-dimethylphenoxy)- 42 g |
| 5 | 400 g | 4-(4-nitro-6-methyl-phenoxy) -phenol 100 g | 220 g | 15 hours | 20° C. | 4-(4-nitro-6-methyl-phenoxy)- 67 g |

It will be appreciated that the instant specification and claims are set forth by way of illustration and not limitation, and that various modifications and changes may be made without departing from the spirit and scope of the present invention

What is claimed is:

1. A process for preparing a difluorochloromethoxybenzene, from a phenol, comprising reacting a phenol of the formula

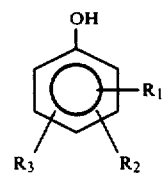

in which

R$_1$, R$_2$ and R$_3$ are identical or different and each stands for hydrogen, halogen, alkyl, aryl, O-aryl or S-aryl with trichloromethyl chloroformate in the presence of hydrogen fluoride, in the absence of a Friedel-Crafts catalyst, wherein the reaction is carried out at a temperature of $-10°$ C. to $+100°$ C., wherein the halogen is selected from the group consisting of fluorine, chlorine, bromine and iodine, wherein the aryl, O-aryl, or S-aryl is an aryl radical containing 6 to 8 C atoms which is unsubstituted or substituted by NO$_2$; CN; COOC$_1$-C$_4$-alkyl; C$_1$-C$_4$-alkyl; fluorine; chlorine; bromine; C$_1$-C$_4$- alkoxy; fluoro-$C_1$-$C_4$-alkyl; chloro-$C_1$-$C_4$-alkyl or bromo-$C_1$-$C_4$-alkyl.

2. A process according to claim 1, wherein one or two of the radicals $R_1$ and $R_3$ stand for hydrogen.

3. A process according to claim 1, wherein the alkyl is $C_1$- to $C_4$-alkyl.

4. A process according to claim 1, wherein $R_1$ is hydrogen;

$R_2$ is hydrogen;

$R_3$ is methyl, fluorine, chlorine, bromine, $C_6$-aryl or O-$C_6$ aryl, said aryl unsubstituted or substituted in the aryl part by $NO_2$; CN; COO$C_1$-$C_4$-alkyl; $C_1$-$C_4$-alkyl; fluorine; chlorine; bromine; $C_1$-$C_4$-alkoxy; fluoro-$C_1$-$C_4$-alkyl; chloro-$C_1$-$C_4$-alkyl or bromo-$C_1$-$C_4$- alkyl.

5. A process according to claim 1, wherein the phenol is selected from the group consisting of 4-chlorophenol, 4-bromophenol, 2-chlorophenol, 2-bromophenol, 2-fluorophenol, 3-fluorophenol, 4-fluorophenol, 3-bromophenol, 4-(4-nitro-2,6-dimethylphenoxy)-phenol, 4-(4-nitro-2,5-dimethylphenoxy)-phenol, 4-(4-nitro-2-chloro-6-methylphenoxy)-phenol, 4-(4-nitro-2-chlorophenoxy)-phenol, 4-(4-nitro-2-chlorophenoxy)-2-chlorophenol, 4-(4-bromophenyl)-phenol and 4-(4-nitrophenyl)-phenol and 4-(4-nitro-6-methylphenoxy)-phenol.

6. A process according to claim 1, wherein 1 to 5 moles of trichloromethyl chloroformate are used per mole of phenol.

7. A process according to claim 1, wherein 5 to 100 moles of hydrogen fluoride are used per mole of phenol.

8. A process according to claim 1, wherein 8 to 40 moles of hydrogen fluoride are used per mole of phenol.

9. A process according to claim 1, which further comprises an inert solvent being used in addition to the hydrogen fluoride.

10. A process according to claim 1, wherein the phenol is added to initially introduced diphosgene.

11. A process according to claim 1, wherein reaction times between 1 and 30 hours are maintained.

* * * * *

UNITED STATES PATENT AND TRADEMARK OFFICE
CERTIFICATE OF CORRECTION

PATENT NO.   : 4,914,244

DATED        : April 3, 1990

INVENTOR(S)  : Albrecht Marhold

It is certified that error appears in the above-identified patent and that said Letters Patent is hereby corrected as shown below:

Title Page      U.S. PATENT DOCUMENTS:  Insert -- 2,516,403, 7/1950, McBee et al. --

Title Page      OTHER PUBLICATIONS:  1st line after " Weygard, " delete " Preparation " and substitute -- Preparative --

Signed and Sealed this

Third Day of September, 1991

Attest:

HARRY F. MANBECK, JR.

*Attesting Officer*          *Commissioner of Patents and Trademarks*